United States Patent [19]

Teicher et al.

[11] Patent Number: 5,295,944
[45] Date of Patent: Mar. 22, 1994

[54] METHOD FOR TREATING A TUMOR WITH IONIZING RADIATION

[75] Inventors: Beverly A. Teicher, Needham; Carl W. Rausch, Medford; Robert E. Hopkins, 2nd, Scituate, all of Mass.

[73] Assignees: Dana-Farber Cancer Institute; Biopure Corporation, both of Boston, Mass.

[21] Appl. No.: 699,761

[22] Filed: May 14, 1991

[51] Int. Cl.$^5$ .............................................. A61N 5/00
[52] U.S. Cl. ........................................ 600/1; 128/898
[58] Field of Search ................................ 600/1-4; 128/897-898

[56] References Cited

U.S. PATENT DOCUMENTS

| | | | |
|---|---|---|---|
| 4,202,323 | 5/1980 | Zweig et al. | 600/4 |
| 4,432,348 | 2/1984 | Nakatsugawa | 600/4 |
| 4,434,788 | 3/1984 | Nakatsugawa | 600/4 |

OTHER PUBLICATIONS

Teicher et al., *Int. J. Radiation Oncol.* 19:27 (1990).
Teicher et al., *Int. J. Radiation Oncol.* 21:969-974 (1991).
Song et al., Increase in pO$_2$ and Radio sensitivity of Tumors by Fluosol-DA and Carbogen, Jan. 1987.
Reiss et al., Solubility and Transport Phenomena in Perfluorochemicals Relevant to Blood Substitution and Other Biomedica Applications, 1982.

*Primary Examiner*—Kyle L. Howell
*Assistant Examiner*—John P. Lacyk
*Attorney, Agent, or Firm*—Hamilton, Brook, Smith & Reynolds

[57] ABSTRACT

A method is disclosed treating a tumor in a host by administering an ultrapurified polymerized hemoglobin solution to the host and thereafter administering ionizing radiation, such as X-rays, to the tumor. In a particularly preferred embodiment, the hemoglobin is bovine hemoglobin.

9 Claims, 2 Drawing Sheets

METHOD FOR TREATING A TUMOR WITH IONIZING RADIATION

GOVERNMENT SUPPORT

Work relating to the invention described and claimed herein was partially supported by Grant No. PO1-19589 from the National Institutes of Health.

BACKGROUND OF THE INVENTION

Solid tumor masses in cancer patients have been found to be heterogeneous in oxygenation and to contain regions of hypoxia. See Vaupel, P., "Oxygenation of Human Tumors", *Strahlenther, Onkol.* 166:377-386 (1990); and Adams, G. E., The Clinical Relevance of Tumour Hypoxia, 26(4):420-421 (1990). Recent studies in human tumors with oxygen electrodes have reaffirmed the occurrence of significant hypoxic areas within human tumors. Vaupel, P. ibid; Kallinowski, F. et al., "Tumor Tissue Oxygenation as Evaluated by Computerized-$pO_2$-Histography", *Int. J. Radiat. Oncol. Biol. Phys.* 19:953-961 (1990); and Gatenby, R. A. et al., "Oxygen Distribution in Squamous Cell Carcinoma Metastases and Its Relationship to Outcome of Radiation Therapy", *Int. J. Radiat. Oncol. Biol. Phys.* 14:831-838 (1988). Preclinical studies, both in vitro and in vivo, have established that hypoxia protects tumor cells from the cytoxic actions of radiation and chemotherapeutic agents and thereby may be a significant factor in therapeutic resistance. Adams, G. E. ibid; Sartorelli, A. C., "Therapeutic Attack of Hypoxic Cells of Solid Tumors: Presidential Address", *Cancer Res.* 48:775-778 (1988); Teicher, B. A. et al., "Classification of Antineoplastic Agents by Their Selective Toxicities Toward Oxygenated and Hypoxic Tumor Cells", *Cancer Res.* 41:73-81 (1981); and Teicher, B. A. et al., "Classification of Antineoplastic Treatments by Their Differential Toxicity Toward Putative Oxygenated and Hypoxic Tumor Subpopulations in vivo in the FSaIIC Murine Fibrosarcoma", *Cancer Res.* 50:3339-3344 (1990).

Increased delivery of oxygen from the lungs can be a useful way of improving the oxygenation of solid tumor masses by altering the gradient of oxygen as it is absorbed from the vasculature and distributed into the tissue. Because of this, one strategy which has been attempted to overcome the problem of hypoxia in treating tumors involves the use of perfluorocarbon emulsions with oxygen or carbogen (95% oxygen/5% carbon dioxide) breathing. Holden, S. A. et al., "Addition of a Hypoxic Cell Selective Cytotoxic Agent (mitomycin C or porfiromycin) to Treatment with Fluosol-DA ®/Carbogen/Radiation", *Radiother. Oncol.* 18:59-70 (1990); Teicher, B. A. et al., "The Effect of Fluosol-DA and Oxygenation Status on the Activity of Cyclophosphamide In Vivo" *Cancer Chemother. Pharmacol.* 21:286-291 (1988); Martin, D. F. et al., "Enhancement of Tumor Radiation Response by the Combination of a Perfluorochemical Emulsion and Hyperbaric Oxygen", *Int. J. Radiat. Oncol. Biol. Phys.* 13:747-751 (1987); Teicher, B. A. and C. M. Rose, "Perfluorochemical Emulsion Can Increase Tumor Radiosensitivity" *Science* 223:934-936 (1984); and Teicher, B. A. et al., "Optimization of Perfluorochemical levels with Radiation Therapy" *Cancer Res.* 49:2693-2697 (1989). In preclinical solid tumor models, the use of perfluorocarbon emulsions with carbogen or oxygen breathing in conjunction with radiation therapy has produced positive results. Teicher, B. A. and C. M. Rose ibid; Teicher, B. A. et al., ibid; Teicher, B. A. and C. M. Rose, "Oxygen-Carrying Perfluorochemical Emulsion as an Adjuvant to Radiation Therapy in Mice", *Cancer Res.* 44:4285-4288 (1984); Teicher, B. A. and C. M. Rose, "Effect of Dose and Scheduling on Growth Delay of the Lewis Lung Carcinoma Produced by the Perfluorochemcial Emulsion, Fluosol-DA", *Int. J. Radiat. Oncol. Biol. Phys.* 12:1311-1313 (1986); Teicher, B. A. et al., "Influence of Scheduling Dose and Volume of Administration of the Perfluorochemical Emulsion Therox ® on Tumor Response to Radiation Therapy", *Int. J. Radiat. Oncol. Biol. Phys.*, in press (1991); Teicher, B. A. et al., "Effect of Fluosol ®-DA on the Response of Intracranial 9L Tumors to X-rays and BCNU", *Int. J. Radiat. Oncol. Biol. Phys.* 15:1187-1192 (1988); Lee. I. et al., "Effects of Fluosol-DA and Carbogen on the Radioresponse of SCK Tumors and Skin of A/J Mice", *Radiat. Res.* 112:173-182 (1987); Martin, D. F. et al., "Effect of a Perfluorochemical Emulsion on the Radiation Response of BA 1112 Rhabdomysarcomas", *Radiat. Res.* 112:45-53 (1987); Moulder, J. E. et al., "Applicability of Animal Tumor Data to Cancer Therapy in Humans", *Int. J. Radiat. Oncol. Biol. Phys.* 14:913-927 (1988); Moulder, J. E. and B. L. Fish, "Tumor Sensitization by the Intermittent use of Perfluorochemical Emulsions and Carbogen Breathing in Fractionated Radiotherapy", In: E. M. Fielden, J. F. Fowler, J. H. Hendry and D. Scott (eds.), Proceedings of the 8th International Congress of Radiation Research, Vol. 1, p. 299, London: Taylor and Francis, Inc. (1987); Rockwell, S. et al., "Reactions of Tumors and Normal Tissues in Mice to Irradiation in the Presence and Absence of a Perfluorochemical Emulsion" *int. Radiat. Oncol. Biol. Phys.* 112:1315-1318 (1986); Song. C. W. et al., "Increase in $pO_2$ and Radiosensitivity of Tumors by Fluosol ®-DA (20%) and Carbogen", *Cancer Res.* 47:442-446 (1987); and Zhang. W. L. et al., "Enhancement of Tumor Response to Radiation by Fluosol-DA", *Int. J. Radiat. Oncol. Biol. Phys.* 10:172-175 (1984).

Further, some initial clinical trials of the perfluorochemical emulsion, Fluosol ®-DA and oxygen breathing with radiation therapy have been carried out and some are still underway. Rose, C. M. et al., "A Clinical Trial of Fluosol ®-DA 20% in Advanced Squamous Cell Carcinoma of the Head and Neck", *Int. J. Radiat. Oncol. Biol. Phys.* 12:1325-1327 (1986); Lustig, R. et al., "Phase I-II Study of Fluosol-DA and 100% Oxygen Breathing as an Adjuvant to Radiation in the Treatment of Advanced Squamous Cell Tumors of the Head and Neck", *Int. J. Radiat. Oncol. Biol. Phys.* 16:1587-1594 (1989); Lustig, R. et al., "Phase I/II Study of Fluosol and 100% Oxygen Breathing as an Adjuvant to Radiation in the Treatment of Unresectable Non Small Cell Carcinoma of the Lung", *Int. J. Radiat. Oncol. Biol. Phys.* 17sl:202 (1989); and Evans, R. G. et al., "A Phase I-II Study of the Use of Fluosol ®-DA 20% as an Adjuvant of Radiation Therapy in the Treatment of Primary High-Grade Brain Tumors", *Int. J. Radiat. Oncol. Biol. Phys.* 1721:175 (1989).

The effect of perfluorocarbon emulsions in carbogen or oxygen breathing with certain chemotherapeutic agents has also been studied in preclinical solid tumor models. Teicher, B. A. et al., "Classification of Antineoplastic Treatments by Their Differential Toxicity Toward Putative Oxygenated and Hypoxic Tumor Subpopulations in vivo in the FSaIIC Murine Fibrosarcoma", *Cancer Res.* 50:3339-3344 (1990); Holden, S. A. et al., "Addition of a Hypoxic Cell Selective Cytotoxic Agent (Mitomycin C or Porfiromycin) to Treatment with Fluosol-DA ®️ Carbogen/Radiation", *Radiother. Oncol.* 18:59-70 (1990); Teicher, B. A. et al., "The Effect of Fluosol-DA and Oxygenation Status on the Activity of Cyclophosphamide in vivo" *Cancer Chemother. Pharmacol.* 21:286-291 (1988); Teicher, B. A. et al., "Approaches to Defining the Mechanism of Fluosol-DA 20%/Carbogen Enhancement of Melphalan Antitumor Activity", *Cancer Res.* 47:513-518 (1987); Teicher, B. A. et al., "Differential Enhancement of Melphalan Cytotoxicity in Tumor and Normal t+Tissue by Fluosol-DA and Oxygen Breathing", *Int. J. Cancer* 36:585-589 (1985); Teicher, B. A. et al., "Effects of Various Oxygenation Conditions on the Enhancement by Fluosol-DA of Melphalan Antitumor Activity", *Cancer Res.* 47:5036-5041 (1987); Teicher, B. A. and S. A. Holden, "A Survey of the Effect of Adding Fluosol-DA 20%/$O_2$ to Treatment with Various Chemotherapeutic Agents", *Cancer Treat. Rep.* 71:173-177 (1987); Teicher, B. A. et al., "Effect of Various Oxygenation Conditions and Fluosol-DA on Cancer Chemotherapeutic Agents", *Biomat., Art. Cells and Art. Organs* 16:533-546 (1988); Teicher, B. A. et al., "Effect of Oxygen on the Cytotoxicity of Antitumor Activity of Etoposide", *J. Natl. Cancer Inst.* 75:1129-1133 (1985); Teicher, B. A. et al., "Effect of Fluosol-DA/$O_2$ on Tumor Cell and Bone Marrow Cytotoxicity of Nitrosoureas in Mice Bearing FSaII Fibrosarcoma", *Int. J. Cancer* 38:285-288 (1986); Teicher, B. A. et al., "Effect of Fluosol-DA/$O_2$ on the Antitumor Activity and Pulmonary Toxicity of Bleomycin", *Cancer Chemother. Pharmacol.* 18:213-218 (1986); Teicher, B. A. et al., "Effects of Fluosol®️-DA and Oxygen Breathing on Adriamycin Antitumor Activity and Cardiac Toxicity in Mice", *Cancer* 61:2196-2201 (1988); Teicher, B. A. et al., "Effect of Carious Oxygenation Conditions and Fluosol®️-Da on the Cytotoxicity and Antitumor Activity of Bleomycin", *J. Natl. Cancer Inst.* 80:599-603 (1988); Teicher, B. A. et al., "Effect of Fluosol-DA/Carbogen on Etoposide/Alkylating Agent Antitumor Activity", *Cancer Chemother. Pharmacol.* 21:281-285 (1988); Martin, D. F. et al., "Potentiation of Rat Brain Tumor Therapy by Fluosol and Carbogen", *NCI Monogr.* 6:119-122 (1988); and Kim. G. E. and C. W. Song, "The Influence of Fluosol-DA and Carbogen Breathing on the Antitumor Effects of Cyclophosphamide In Vivo", *Cancer Chemother. Pharmacol.* 25:99-102 (1989). With many chemotherapeutic agents, very positive therapeutic results have been obtained and several initial clinical trials have been carried out with Fluosol-DA and oxygen breathing with single anticancer drugs. See Gruber, M. et al., "Phase I/II Study of Fluosol®️/$O_2$ in Combination with BCNU in Malignant Glioma", *Proc. Amer. Assoc. Cancer Res.* 31:190 (March 1990); Carewal, H. et al., "Fluosol®️/Oxygen in Combination with Cyclophosphamide in Advanced Non-Small Cell Lung Carcinoma (NSCLC): Phase I Results", *Proc. Amer. Assoc. Cancer Res.* 30:271 (March 1989); and Meyers, F. et al., "Phase I/II Study of Fluosol®️/Oxygen in Combination with Weekly 5-Fluorouracil (5FU) in Metastatic Colorectal Carcinoma", *Proc. Amer. Assoc. Cancer Res.* 30:256 (March 1989).

Despite the initial success with the use of perfluorocarbon emulsions and carbogen or oxygen breathing in conjunction with ionizing radiation, these techniques have not proven entirely satisfactory. For example, perfluorocarbons have very limited oxygen-transport capability at ambient oxygen pressures. Blood delivers approximately 6% (v/v) oxygen to tissues at ambient pressures, whereas, at these same pressures, perfluorocarbon emulsions can only deliver about 2% (v/v).

SUMMARY OF THE INVENTION

This invention relates to a method for treating a tumor in a host, including a human being, with ionizing radiation. In this method, an ultrapurified polymerized hemoglobin solution (UPHS) is administered to the host in an amount which significantly increases the antitumor effect of the ionizing radiation. An effective amount of the ionizing radiation is also administered to the host. In a particularly preferred embodiment, the hemoglobin is bovine hemoglobin.

Administering an ultrapurified polymerized hemoglobin solution with administration of the ionizing radiation significantly increases the antitumor effect of the radiation. In addition, the use of the hemoglobin solution, in contrast to the use of perfluorocarbon emulsions, has certain advantages. Hemoglobin is able to chelate and deliver oxygen under air-breathing conditions. Polymerized hemoglobins have a longer circulating half-life than many of the perfluorocarbon emulsions and, therefore, have a longer functional period post-administration. The acidic environments in tumors increases the off-loading of oxygen and, therefore, the oxygen delivery from hemoglobin, as should temperature elevation (i.e., clinical hypothermia). Hemoglobin solutions also have less retention in normal tissues, which is a concern with many perfluorocarbon preparations.

DETAILED DESCRIPTION OF THE INVENTION

Figure 1:
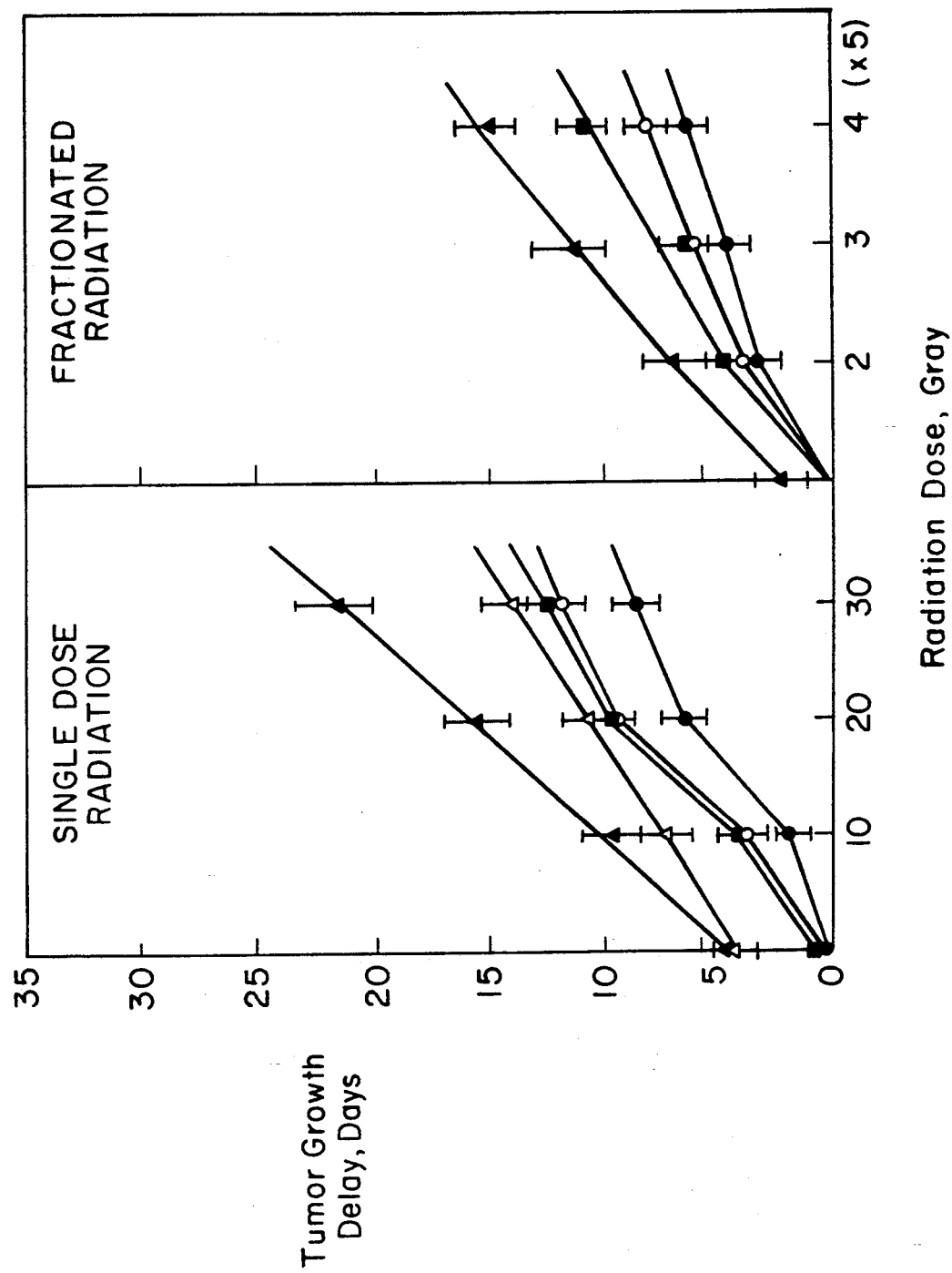
FIG. 1 is a plot of the tumor growth delay of the Lewis lung carcinoma produced by single dose or fractionated radiation treatment with or without previous administration of ultrapurified polymerized bovine hemoglobin solution (UPBHS) and air breathing or carbogen breathing versus radiation dose.

This invention relates to a method for treating a tumor in a host. The host can be any species which develops solid tumors. Examples of hosts include but are not limited to, reptiles, amphibians, avians and mammals, including human beings, as well as domestic animals such as dogs, cats, cows and horses.

Tumors treatable by this method include those in which oxygen heterogeniety, including regions of hypoxia, protect tumor cells against the cytotoxic action of ionizing radiation. These are usually solid tumors, such as sarcomas, carcinomas, lymphomas, etc. However, in certain cases of dispersed tumor cells, such as advanced leukemia, masses of tumor cells form which can produce regions of oxygen heterogeneity, as well.

Any type of ionizing radiation which exhibits an antitumor effect can be employed with this invention. Some examples include X-rays, gamma rays, high-energy electrons and High LET radiation, such as protons, neutrons and alpha particles.

The ionizing radiation is employed by techniques well-known to those skilled in the art. For example, X-rays and gamma rays are applied by external and/or interstitial means from linear accelerators or radioactive sources. High energy electrons can be produced by linear accelerators. High LET radiation is also produced by linear accelerators and can also be applied from radioactive sources implanted interstitially.

Dosages of the ionizing radiation are those conventionally applied in radiotherapeutic treatment of tumors. In certain cases, it might be that use of UPHS in conjunction with ionizing radiation might lower the dosage of ionizing radiation required.

In order to increase oxygen transport to the site of a tumor, an ultrapurified polymerized hemoglobin solution (UPBHS) is administered to the host. Although not essential, it is preferred to administer the UPHS prior to administration of the antitumor agent. Also, the hemoglobin solution is preferably administered intravenously so that it is taken up into the bloodstream of the host immediately.

As mentioned above, it is preferably to administer UPHS prior to administration of the chemotherapeutic agent. The amount of time between the administration of the hemoglobin solution and chemotherapeutic agent will depend upon factors such as the amount of time it takes the hemoglobin solution to be fully incorporated into the circulatory system of the host, the lifetime of the hemoglobin solution, etc. Since polymerized bovine hemoglobin has been found to remain in the host's blood stream for up to at least 48 hours, anytime during this period is sufficient.

Hemoglobin sufficient for the hemoglobin solutions can be derived from a wide variety of sources. These sources include human blood, such as outdated blood bank supplies. Additionally, the hemoglobin can be derived from a variety of mammalian sources such as horses, pigs, cows, sheep, etc.

In a preferred embodiment, the hemoglobin will be derived from a species in which the hemoglobin is chloride ion-dependent for oxygen transport rather than dependent upon 2,3-diphosphoglycerate (2,3-DPG) or other phosphate molecules. This is because 2,3-DPG, present in human red blood cells, is not available freely in the circulatory system of the host to effect oxygen uptake and release for hemoglobin solutions administered according to this invention. Thus, it is preferred to employ a hemoglobin which is chloride ion-dependent for oxygen transport, such as those hemoglobins derived from sheep, goats, cows and cats. See Bunn, H. F., "Differences in the Interaction of 2,3-Diphosphoglycerate with Certain Mammalian Hemoglobins", Science 172:1049-50 (1971); Breepoel, P. M. et al., "Interaction of Organic Phosphates with Bovine Hemoglobin—I Oxylabile and Phosphate Labile Proton Binding", Pflugers Arch. 389:219-25 (1981); and Fronticelli, C. et al., "Solvent Regulation of Oxygen Affinity and Hemoglobin—Sensitivity of Bovine Hemo-Globin to Chloride Ions", J. Biol. Chem. 259:10841-4 (1984). Bovine hemoglobin is particularly preferred because of its proven ability to transport oxygen in human beings and other mammals, in a chloride ion-dependent way, and because of its low antigenicity in human beings when it has been ultrapurified.

In order to increase the useful life of hemoglobin in the circulation, it is polymerized or crosslinked by a variety of techniques. Crosslinking agents include dialdehydes, such as glyoxal, malonic dialdehyde, succinic dialdehyde, glutaraldehyde, adipaldehyde, 3-methylglutaraldehyde, propyladipaldehyde, phthalic dialdehyde, terephthaldehyde and malonic dialdehyde have been employed. See, in this regard, Bonsen et al., U.S. Pat. Nos. 4,001,200; 4,001,401; and 4,053,590; Bonhard et al., U.S. Pat. Nos. 4,136,093 and 4,336,248; the teachings of each of which are incorporated herein by reference.

The polymerized hemoglobin solution is ultrapurified by various filtration and chromatographic procedures which have been described heretofore in the art. An ultrapure hemoglobin solution, according to this invention, is a hemoglobin solution which is substantially free of stroma, endotoxin, other pyrogenic substances, phospholipids, immunoglobulins and cellular-contained enzymes.

A particularly preferred ultrapure polymerized hemoglobin solution is based upon bovine hemoglobin. Such a bovine blood substitute has an endotoxin concentration of less than 0.5 endotoxin units/ml as measured by the LAL test; a phospholipid concentration of less than about 1 nanogram/milliliter and has a molecular weight distribution greater than 90% in the range of 68,000–500,000 daltons. This bovine hemoglobin solution also has an osmolarity measured by freezing point depression in the range of 180–320 milliosmols per liter; a hemoglobin content of 5–25 grams per deciliter; a met hemoglobin content of less than 20%; a $P_{50}$ in the range of 18–36 mmHg; an intravascular half life of at least two days; a crosslinking profile on gel permeation chromatography of 50–70%.

Such ultrapurified polymerized bovine hemoglobin solution is made and sold by Biopure Corporation, Boston, Mass. under the trademark Hemopure. This and other ultrapurified hemoglobin solutions are described in International Patent Application PCT/US87/02967, published under WO88/03408, the teachings of which are hereby incorporated by reference.

Appropriate dosages of UPBHS can be determined by those skilled in the art using routine experimentation. The dose employed in the murine studies in the Examples herein was 12 ml/kg, which is 13%–15% of the estimated circulatory volume, or 1.32 g protein/kg. This dose corresponds to 840 ml as the comparative human dose or 17%–19% of estimated circulatory volume, and 92.4 g protein in a 70 kg person. Multiple doses of UPHS, for example one before each radiation treatment, are, of course, useful with this invention and can be preferred in many cases.

Although not required, it is preferred to have the host breath oxygen-enriched gas prior to and post administration of the ionizing radiation. This can be done by having the host breath oxygen-enriched air, 100% oxygen or carbogen (95% oxygen/5% $CO_2$), or in certain cases exposing the host to hyperbaric oxygen conditions.

The techniques for treating tumors described herein can be employed at normal body temperatures or at elevated body temperatures (hypothermia).

This invention will now be further and more specifically described by the following examples.

EXAMPLE I

Tumor Growth Delay with UPBHS or Perfluorocarbons Used in Conjunction with Gamma Ray Irradiation The Lewis lung tumor model was employed. Shipley, W. V. et al., "Tumor Size Dependence in the Radiation Response of the Lewis lung carcinoma", *Cancer Res.* 35:2488-2493 (1975); Stanley, J. A. et al., "Influence of Tumor Size on Hypoxic Fraction and Therapeutic Sensitivity of Lewis Lung Tumor", *Br. J. Cancer* 36:105-113 (1977); and Steel, G. G. et al., "Combined Radiotherapy-Chemotherapy of Lewis Lung Carcinoma", *Int. J. Radiat. Oncol. Biol. Phys.* 4:49-52 (1978). When the tumors were approximately 100 mm$^3$ in volume, Fluosol-DA (2.4 g PFC/kg, 0.3 ml), F44E at doses of 2 g PFC/kg (0.2 ml), 4 g PFC/kg (0.2 ml), or 8 g PFC/kg (0.2 ml), or UPBHS (Hemopure blood-substitute solution) (0.3 ml) was injected into the tail vein of the mice and air or carbogen breathing was begun.

Fluosol-DA 20% was obtained from Alpha Therapeutics Corp., Los Angeles, Calif. The stem emulsion consists of 25% (w/v) perfluorochemicals: 7 parts perfluorodecalin; 3 parts perfluorotripropyliamine; Pluronic F-68 (2.7%, w/v); yolk phospholipids (0.4%, w/v) as emulsifiers; and glycerol (0.8%, w/v) as a cryoprotective agent. the annex solution (electrolyte/bicarbonate solution) furnished the preparation with physiological osmolarity. the half-life of Fluosol-DA in vivo is about 12 hours. Geyer, R. P., "Substitutes for Blood and Its Components" In: Jamieson, G. A. and T. J. Greenwalt, eds., *Blood Substitutes and Plasma Expanders*, New York, N.Y.: Liss pp. 1-21 (1978).

The F44E perfluorochemical emulsion, Therox (E. I. Du Pont de Nemours & Co., Chemicals and Pigments Dept., Deepwater, N.J.), contains 48% (v/v, 83% w/v) F44E and egg yolk lecithin as the emulsifier in an isotonic buffer was used as the perfluorochemical source. The particle size of the emulsion is 0.25 $\mu$M. The half-life of this emulsion in circulation is about 2.5 hours and the dwell time of this perfluorochemical in tissues is about 7 days. Riess, J. G., "Reassessment of Criteria for the Selection of Perfluorochemicals for Second-Generation Blood Substitutes. Analaysis of Structure/Property Relationships", *Artif. Organs (Cleve.)* 8:44-56 (1984); and Riess, J. G. and M. LeBlanc, "Soluability and Transport Phenomena in Perfluorochemicals Relevant to Blood Substitution and Other Biomedical Applications", *Pure Appl. Chem.* 54:2383-2406 (1982).

Hemopure blood-substitute solution is the polymerized form of a highly purified bovine hemoglobin solution. Hemopure solution contains 11±2 gm/deciliter of bovine hemoglobin. Greater than 50% (w/v) of the hemoglobin has a molecular weight greater than 68,000 and up to 500,000, and less than 10% (w/v) has a molecular weight less than or equal to 68,000. Hemopure solution also contains sodium (120±20 mM/L), chlorine (115±25 mM/l), and potassium (4.0±1 mM/L) in this buffer (pH 7.8±0.4). The circulating half-life of the Hemopure solution is about 2.5 days. DeVenuto, F., "Evaluation of Human and Bovine Modified-Hemoglobin Solution as Oxygen Carrying Fluid for Blood Volume Replacement", *Biomaterials, materials, Articial Cells, and Artificial Organs* V. 16, Nos. 1-3:77-84 (1988); and Winslow, R. M., "Optimal Hematologic Variables for Oxygen Transport Including P50, Hemoglobin Cooperativity, Hematocrit, Acid-Base Status, and Cardiac Function", *Biomaterials, Articial Cells, and Artificial Organs*, V. 16, Nos. 1-3:149-172 (1988).

Carbogen breathing was maintained for 1 hour before and during delivery of each radiation fraction for those groups receiving carbogen, using $^{137}$Cs gamma rays locally (Gamma Cell 40, Atomic Energy of Canada, Ltd.) to the tumor-bearing limb (dose rate, 0.88 Gy/min.). The animals were irradiated unanesthesized in an apparatus which allowed local treatment of the tumor-bearing limb. The animals received less than 2% of the total dose whole body. In the fractionated radiation regimen, 2, 3, or 4 Gray were delivered daily for 5 days, ± daily treatment with the various oxygen-carrying solutions. In the single dose radiation regimen, the radiation doses were 10, 20 or 30 Gray. Tumor size was ascertained by thrice-weekly measurements with calipers. The experimental end point was the number of days post-tumor cell implantation for the tumors to reach a volume of 500 mm$^3$. Schabel, Jr., F. M. et al., "Testing Therapeutic Hypotheses in Mice and Man: Observations on the Therapeutic Activity Against Advanced Solid Tumors of Man", *Methods Cancer Res.* 17:3-51 (1979). Untreated tumors reach 500 mm$^3$ in approximately 14 days. Each experimental group had 7 mice and each experiment was repeated at least once; therefore, the minimum bnumber of tumors examined at each point was 14. Teicher, B. A. and C. M. Rose, "Perflurochemical Emulsions Can Increase Tumor Radiosensitivity", *Science* 223: 934-936 (1984).

Data from the tumor growth delay experiments were analyzed using a computer program written in BASIC. The program first derives the best-fit curve for each individual set of tumor volume data and then calculates the median, mean, and standard error on the day the tumor reach 500 mm$^3$. Dose modifying factor was calculated as the ratio of the slopes of the tumor growth delay or tumor cell survival curves in the presence or absence of the perfluorochemical emulsion or PBHS.

The dose modifying factors calculated for these radiation treatment regimens are shown in the following Table.

Dose Modifying Factors Observed in the Lewis Lung Carcinoma Treated with Perfluorochemical Emulsions or with UPBHS and Various Levels of Oxygen[a]

| Oxygen Carrier | Dose, g/kg (ml/kg) | % Oxygen Atmosphere | | | |
|---|---|---|---|---|---|
| | | 20% | 65% | 85% | 95% |
| Fluosol-DA | 2.4 (12) | 1.0[b] | 1.0 | 1.3 | 2.1 |
| F44E | 2.0 (8) | 1.0 | 1.0 | 1.0 | 1.9 |
| | 4.0 (8) | 1.0 | 1.0 | 1.0 | 2.2 |
| | 8.0 (8) | 1.0 | 1.25 | 1.3 | 1.8 |
| PBHS | 1.32 (12) | 1.6 | — | — | 2.1 |

[a] Dose modifying factors were calculated as the ratio of the slopes of the tumor growth delay curves in the presence or absence of the perfluorochemical emulsions or hemoglobin preparation for animals breathing each atmosphere. X-ray doses were 2, 3 or 4 gy daily for 5 days locally to the tumor.
[b] 1.0 = no effect.

Fluosol-DA was administered at the optimal dose for that perfluorochemical emulsion of 2.4 g PFC/kg (0.3 ml, 12 ml/kg). Fluosol-DA administration did not significantly alter the response of the tumors to the radiation treatments when air or 65% oxygen was breathed, but there was a small benefit from Fluosol-DA if an atmosphere of 85% oxygen was breathed. A dose modifying factor of 2.1 was obtained when carbogen (95% O$_2$, 5% CO$_2$) was used, indicating substantial enhancement of tumor growth delay with Fluosol-DA/carbogen/radiation compared with carbogen/radiation.

The perfluorochemical emulsion preparation, F44E, is much more concentrated than Fluosol-DA, allowing a dosage range of perfluorochemical to be examined. An F44E dose of 0.2 ml allowed a dose of 8 g PFC/kg to be administered, and dilutions with phosphate buffered 0.9% saline were used to achieve the doses of 4 g PFC/kg and 2 g PFC/kg each at 8 ml/kg (i.e., in 0.2 ml). Administration of the two lower doses of the F44E perfluorochemical emulsion did not alter the response of the tumor to the fractionated radiation regimen if air, 65% oxygen, or 85% oxygen was breathed; however, if 95% oxygen was breathed, a dose modifying factor of 1.9 was obtained with 2 g PFC/kg of F44E, and a dose modifying factor of 2.2 was obtained with 4 g PFC/kg of F44E. At the highest dose of perfluorochemical emulsion of 8 g PFC/kg of F44E, although there was no increase in tumor growth delay produced by radiation when air was breathed, small degree of dose modification was obtained when atmospheres of 65% and 85% oxygen were breathed, and a dose modifying factor of 1.8 was obtained when carbogen was breathed (Table 1).

Daily administration of 1.32 g protein/kg (0.3 ml, 12 ml/kg) of UPBHS along with air breathing and fractionated radiation therapy produced a significant enhancement of tumor growth delay, resulting in a dose modifying factor of 1.6. When the UPBHS administration was accompanied by carbogen breathing, there was a further increase in tumor growth delay, so that the dose modifying factor increased to 2.2.

Shown in FIG. 1 is the tumor growth delays of the Lewis lung carcinoma produced by single dose and fractionated radiation and UPBHS with air breathing or carbogen breathing. For single dose radiation, the symbols in FIG. 1 are defined as follows: " " represents radiation/carbogen, "o" is 0.5 mL of UPBHS with air, " " is 0.3 mL of UPBHS at with air, "Δ" is 0.5 mL of UPBHS with carbogen, and " " is 0.3 mL of UPBHS with carbogen.

Similarly, the symbols in FIG. 1 for fractionated radiation are as follows: " " represents radiation/carbogen, "o" is 0.3 mL of UPBHS on days 1, 3, 5 with radiation, " " is 0.3 mL of UPBHS on days 1-5 with radiation, and " " is 0.3 ml of UPBHS on days 1-5 with radiation and carbogen. Data in FIG. 1 are the means of two independent experiments (n=14). The bars are S.E.M. When UPBHS either 0.5 ml or 0.3 ml was administered 1 hour before radiation treatment and the animals were maintained with air breathing, a dose modifying factor of 1.5-1.6 was obtained. When the same UPBHS treatments were followed by 1 hour of carbogen breathing before and during radiation delivery, a dose modifying factor of 2.0-2.1 was obtained with 0.5 ml of UPBHS, and a dose modifying factor of 3.8-4.0 was obtained with 0.3 ml of UPBHS. In effect UPBHS and carbogen breathing resulted in 3.9±0.5 days of tumor growth delay in the absence of radiation treatment. When UPBHS (0.3 ml) was administered on alternate days of a daily fractionated radiation regimen with air breathing, a dose modifying factor of 1.3-1.4 was obtained. However, if UPBHS (0.3 ml) was administered daily 1 hour before each radiation faction with air breathing, a dose modifying factor of 1.6-1.7 was obtained. If daily carbogen breathing was added to the treatment with daily UPBHS and fractionated radiation, a dose modifying factor of 2.0-2.2 was obtained.

EXAMPLE II

Tumor Cell Survival with UPBHS Used in Conjunction with X-Rays

Tumor cell survival assay was carried out using the FsaIIC fibrosarcoma. The FSaII fibrosarcoma (Rice, L. et al., "The Radiosensitivity of a Murine Fibrosarcoma as Measured by Three Cell Survival Assays", *Br. J. Cancer* 41: 240-245 (1980)) adapted for growth in culture (FSaIIC) (Teicher, B. A. and C. M. Rose, "Perfluorochemical Emulsions Can Increase Tumor Radiosensitivity", *Science* 223:934-936 (1984)) was carried in C3H/FeJ male mice. $2 \times 10^6$ tumor cells prepared from a brei of several stock tumors were implanted intramuscularly into the legs of C3H/FeJ male mice 8-10 weeks of age.

Figure 2:
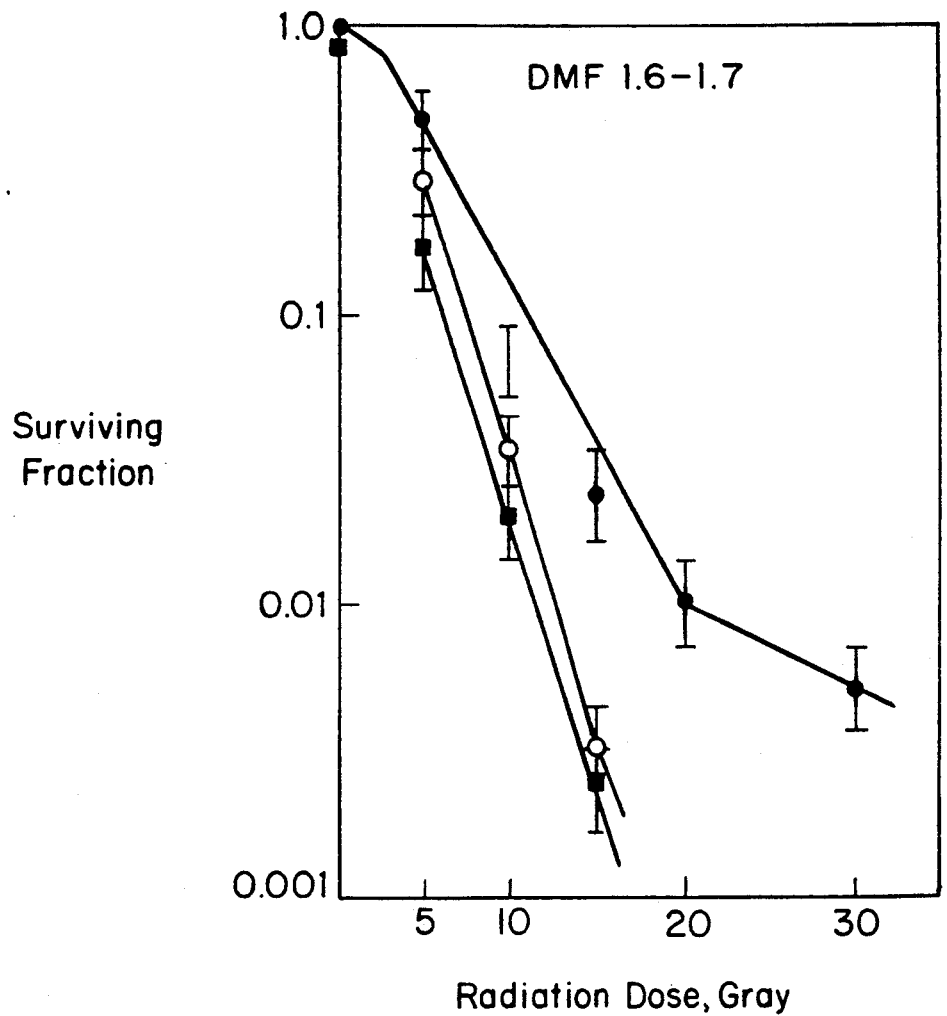
FIG. 2 is a plot of the surviving fraction of FSaIIC cells from FSaIIC tumors treated in vivo with single doses of radiation with and without prior administration of UPBHS versus radiation dose.

When the FSaIIC tumors were approximately 100 $mm^3$ in volume (about 1 week after tumor cell implantation), animals were treated with single doses of X rays at 5, 10, 15 or 20 Gy alone or preceded by UPBHS, (0.3 or 0.5 ml) administered via tail vein injection. Mice were killed 24 hours after treatment to allow for full expression of radiation cytotoxicity and repair of potentially lethal damage and then immersed in 95% ethanol. The tumors were excised under sterile conditions, and single cell suspensions were prepared for the colony-forming assay. Teicher, B. A. et al., "Approaches to Defining the Mechanism of Fluosol-DA 20% with Carbogen Enhancement of Melphalan Antitumor Activity", *Cancer Res.* 47: 513-518 (1987); and Teicher, B. A. and C. M. Rose, "Perfluorochemical Emulsions Can Increase Tumor Radiosensitivity", *Sceicen* 223:934-936 (1984). The cell yields were $18.3\pm4.1\times10^6$ per tumor. One week later, the plates were stained with crystal violet, and colonies of more than 50 cells were counted. The untreated tumor cell suspensions had a plating efficiency of 8%-12%. The results are expressed as the surviving fraction±SE of cells from untreated groups compared with shown in FIG. 2 is the survival of FSaIIC cells from FsaIIC tumors treated in vivo under various conditions. The symbols are defined as follows: " " represents FSaIIC tumors treated with single doses of radiation. FSaIIC tumors treated with 0.3 mL of UPBHS and radiation is "O". Further, " " represents FSaIIC tumors treated with 0.5 ml of UPBHS and radiation. Data in FIG. 2 are the means of three independent experiments. Bars are S.E.M.

The radiation dose survival curve for the untreated FSaIIC tumor biphasic indicating two tumor subpopulations. The more sensitive cells on the first part of the curve may be the oxygenated cells and the less sensitive cells on the second part of the curve may be the hypoxic cells. When UPBHS (0.3 or 0.5 ml) was administered 1 hour before radiation treatment, a dose modifying factor of 1.5-1.7 was obtained compared with radiation and carbogen breathing.

Equivalents

Those skilled in the art will recognize or be able to ascertain, using no more than routine experimentation, many equivalents to the specific embodiments of the invention described herein. Such equivalents are intended to be covered by the following claims.

We claim:
1. A method for treating a tumor in a host with ionizing radiation, comprising:

a) administering to said host an ultrapurified polymerized hemoglobin solution in an amount sufficient to increase the antitumor effect of said ionizing radiation; and, b) administering to said tumor an effective amount of said ionizing radiation.

2. A method of claim 1 wherein said ionizing radiation comprises X-rays, gamma rays, electrons or high LET radiation.

3. A method of claim 1 wherein said ultrapurified polymerized hemoglobin solution comprises a hemoglobin which is dependent upon chloride ion concentration for oxygen transport.

4. A method of claim 1 wherein said ultrapurified polymerized hemoglobin solution is bovine hemoglobin.

5. A method of claim 4 wherein said ionizing radiation comprises X-rays, gamma rays, electrons or high LET radiation.

6. A method of claim 1 wherein said host is a mammal.

7. A method of claim 6 wherein said mammalian host is a human being.

8. In a method of treating a tumor in a mammalian host with ionizing radiation the improvement comprising:

administering to said mammalian host, prior to treatment with said ionizing radiation, an ultrapurified bovine hemoglobin solution in an amount sufficient to increase the antitumor effect of said ionizing radiation.

9. The improvement of claim 8 wherein said mammalian host comprises a human being.

* * * * *